United States Patent [19]
McGrath et al.

[11] Patent Number: 6,123,083
[45] Date of Patent: Sep. 26, 2000

[54] DEVICE AND METHOD FOR TREATMENT OF A PROSTATE WHILE PREVENTING URETHRAL CONSTRICTION DUE TO COLLAGEN RICH TISSUE SHRINKAGE

[75] Inventors: Jonathan R. McGrath, Chanhassen, Minn.; Mitchell Dann, Jackson, Wyo.

[73] Assignee: Urologix, Inc., Minneapolis, Minn.

[21] Appl. No.: 08/920,744

[22] Filed: Aug. 29, 1997

[51] Int. Cl.⁷ .................................................. A61B 19/00
[52] U.S. Cl. ........................... 128/898; 607/40; 607/101; 607/116
[58] Field of Search ................................ 128/898; 607/1, 607/40, 101, 116

[56] References Cited

U.S. PATENT DOCUMENTS

| | | | |
|---|---|---|---|
| 4,643,186 | 2/1987 | Rosen et al. | 128/303.1 |
| 4,709,698 | 12/1987 | Johnston et al. | 128/303.12 |
| 4,799,479 | 1/1989 | Spears | 128/303.1 |
| 4,808,164 | 2/1989 | Hess | 604/95 |
| 5,007,437 | 4/1991 | Sterzer | 428/786 |
| 5,057,106 | 10/1991 | Kasevich et al. | 606/33 |
| 5,061,267 | 10/1991 | Zeiher | 606/40 |
| 5,151,100 | 9/1992 | Abele et al. | 606/28 |
| 5,234,004 | 8/1993 | Hascoet et al. | 607/116 |
| 5,304,214 | 4/1994 | DeFord et al. | 607/105 |
| 5,344,398 | 9/1994 | Hara | 604/96 |
| 5,366,490 | 11/1994 | Edwards et al. | 607/99 |
| 5,391,196 | 2/1995 | Devonec | 607/96 |
| 5,484,384 | 1/1996 | Fearnot | 600/3 |
| 5,496,271 | 3/1996 | Burton et al. | 604/54 |
| 5,531,676 | 7/1996 | Edwards et al. | 604/22 |
| 5,800,378 | 9/1998 | Edwards et al. | 604/22 |
| 5,843,144 | 12/1998 | Rudie et al. | 607/101 |

FOREIGN PATENT DOCUMENTS

| | | |
|---|---|---|
| 0 335 022 A1 | 3/1988 | European Pat. Off. |
| WO 91/11975 | 8/1991 | WIPO . |
| 92/04934 | 4/1992 | WIPO . |
| 92-07621 | 5/1992 | WIPO . |
| 93/04727 | 3/1993 | WIPO . |
| 95/01814 | 1/1995 | WIPO . |
| 97/01374 | 1/1997 | WIPO . |
| 97/24992 | 7/1997 | WIPO . |

OTHER PUBLICATIONS

Krivoborodov, G. G., The temperature regiments for transurethral thermotherapy in treating benign prostatic hyperplasia, Urologiia I Nefrologiia, (3) 36–8, May 1997.
Sturesson et al., Theoretical analysis of transurethral laser–induced thermo–therapy for treatment of benign prostatic hyperplasia, Phys. Med. Biol. (41) 445–463, Mar. 1996.
Kaplan, Steven, A., et al., State of the art: microwave therapy in the management of men with benign prostatic hyperplasia: current status, Journal of urology, (150) 1597–602, Nov. 1993.
Agah, Ramtin, et al., Rate process model for arterial tissue thermal damage: implications on vessel photocoagulation, Lasers in surgery and Medicine, (15) 176–184, 1994.

*Primary Examiner*—Mickey Yu
*Assistant Examiner*—Dinh X. Nguyen
*Attorney, Agent, or Firm*—Kinney & Lange, P.A.

[57] ABSTRACT

Tissue surrounding a bodily conduit, such as a urethra, is thermally treated while preventing restrictions of the bodily conduit due to heat-induced shrinkage of collagen rich tissue surrounding the bodily conduit. A select volume of collagen-containing tissue surrounding the urethra is heated to destroy the tissue and to cause the tissue to be capable of being plastically remodeled into a selected shape. The selected shape is defined while the tissue is heated, and the tissue is allowed to cool while continuing to define the selected shape to cause plastic remodeling of the tissue into the selected shape. The method also includes performing a thermal therapy treatment without causing the surrounding tissue to exceed a collagen transition temperature of the tissue during the heating step of the treatment session.

6 Claims, 13 Drawing Sheets

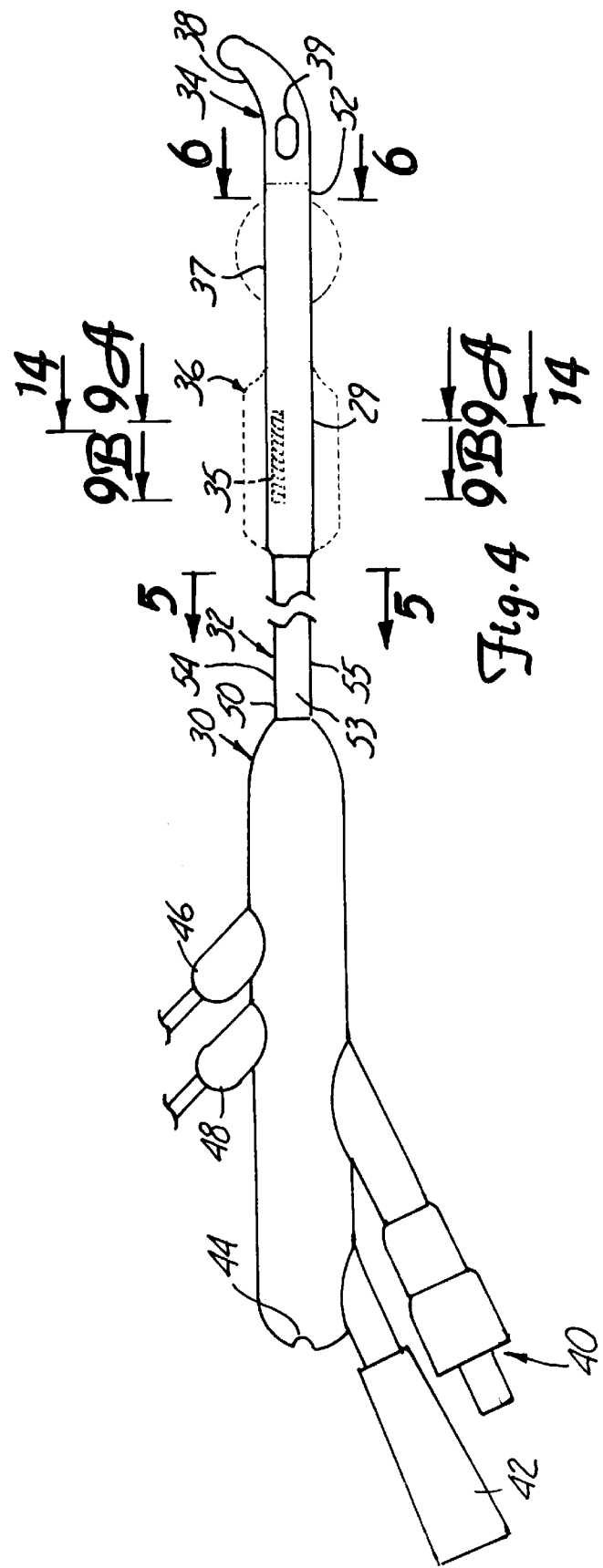

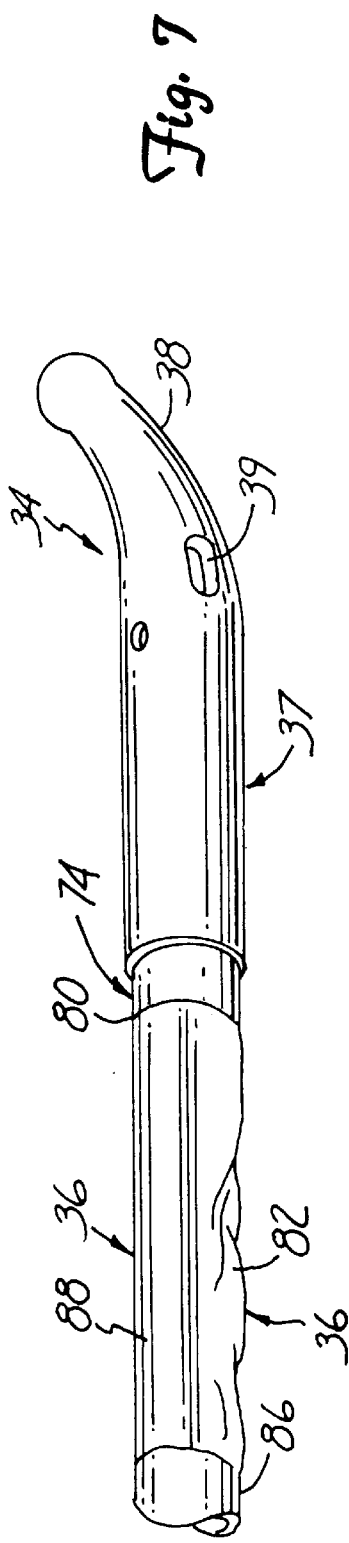
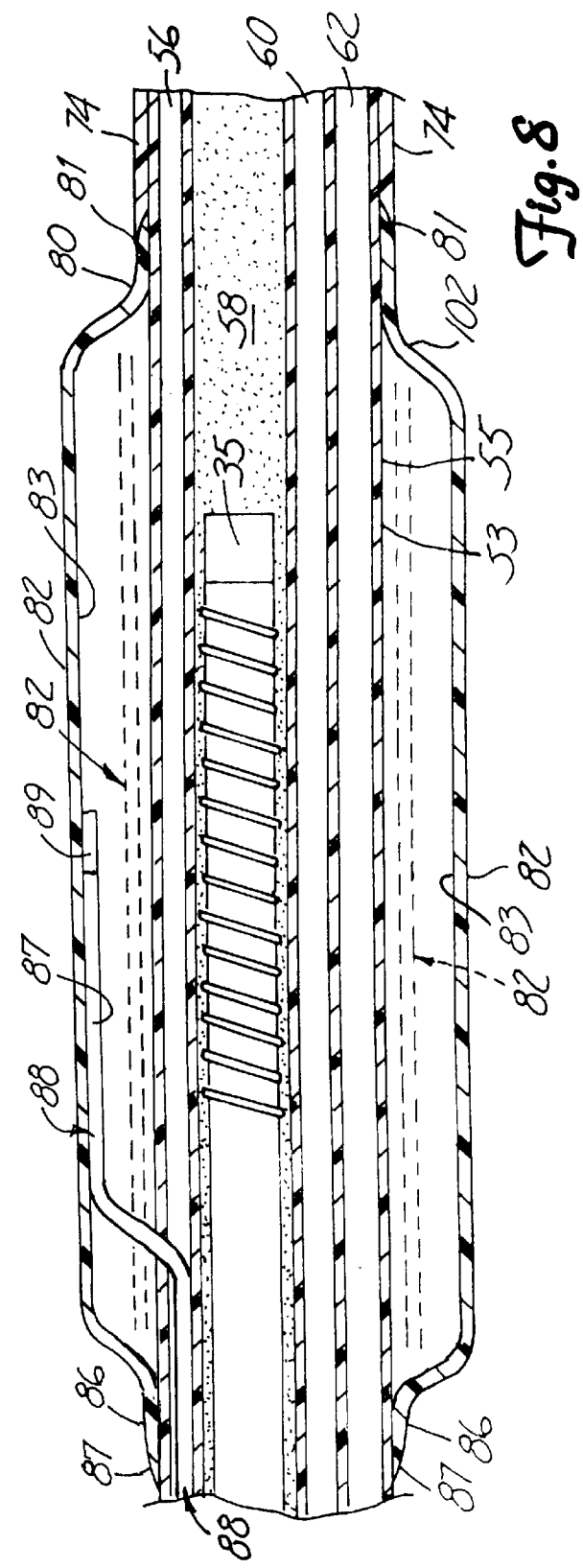

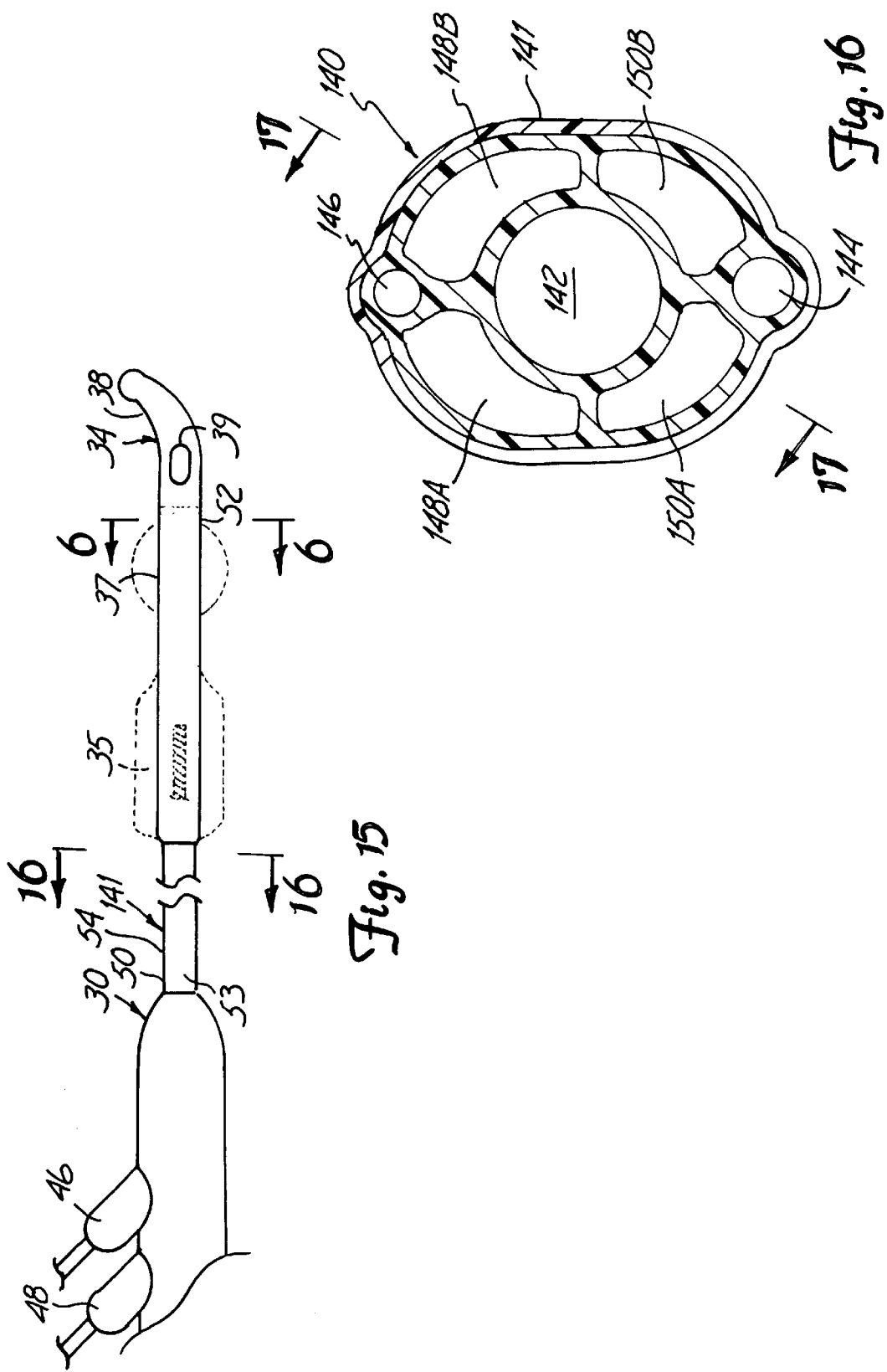

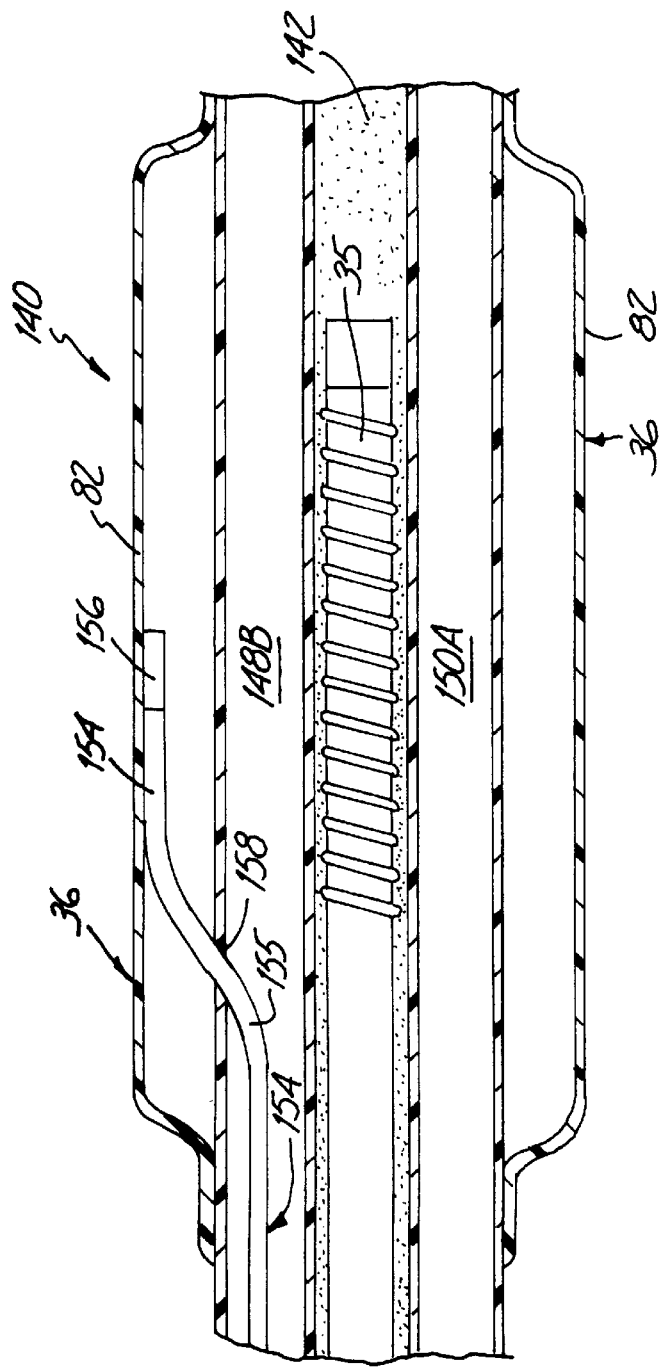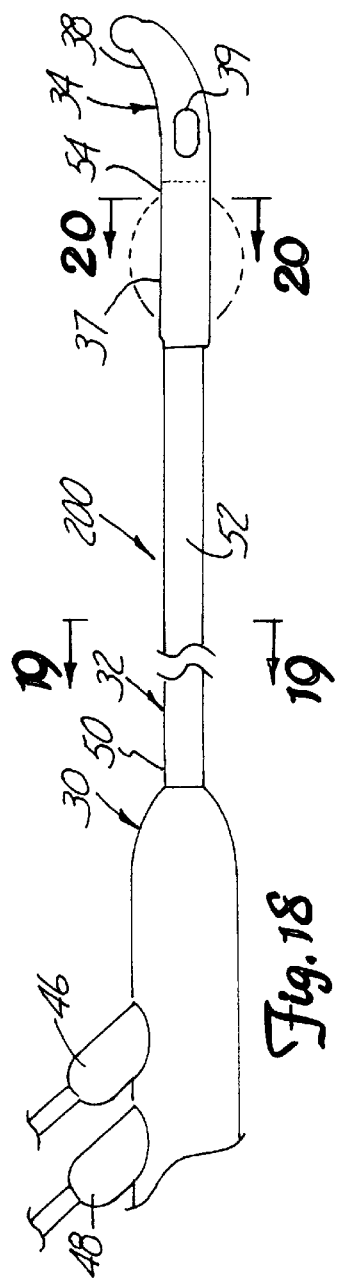
Fig. 17
Fig. 18

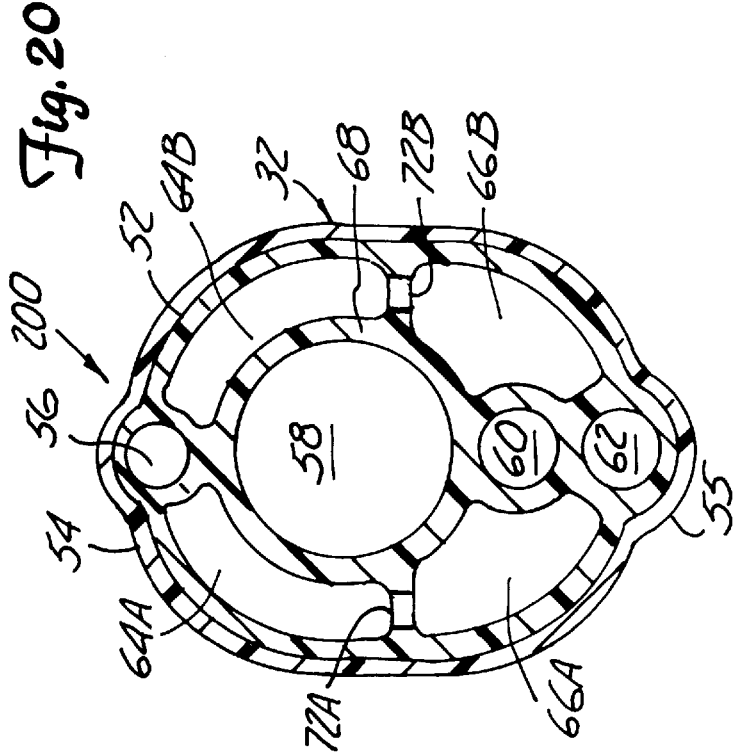
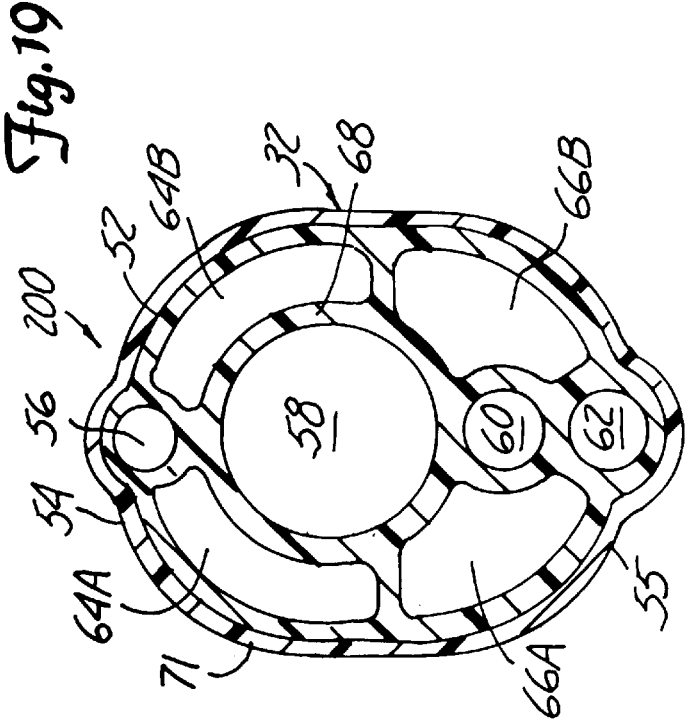

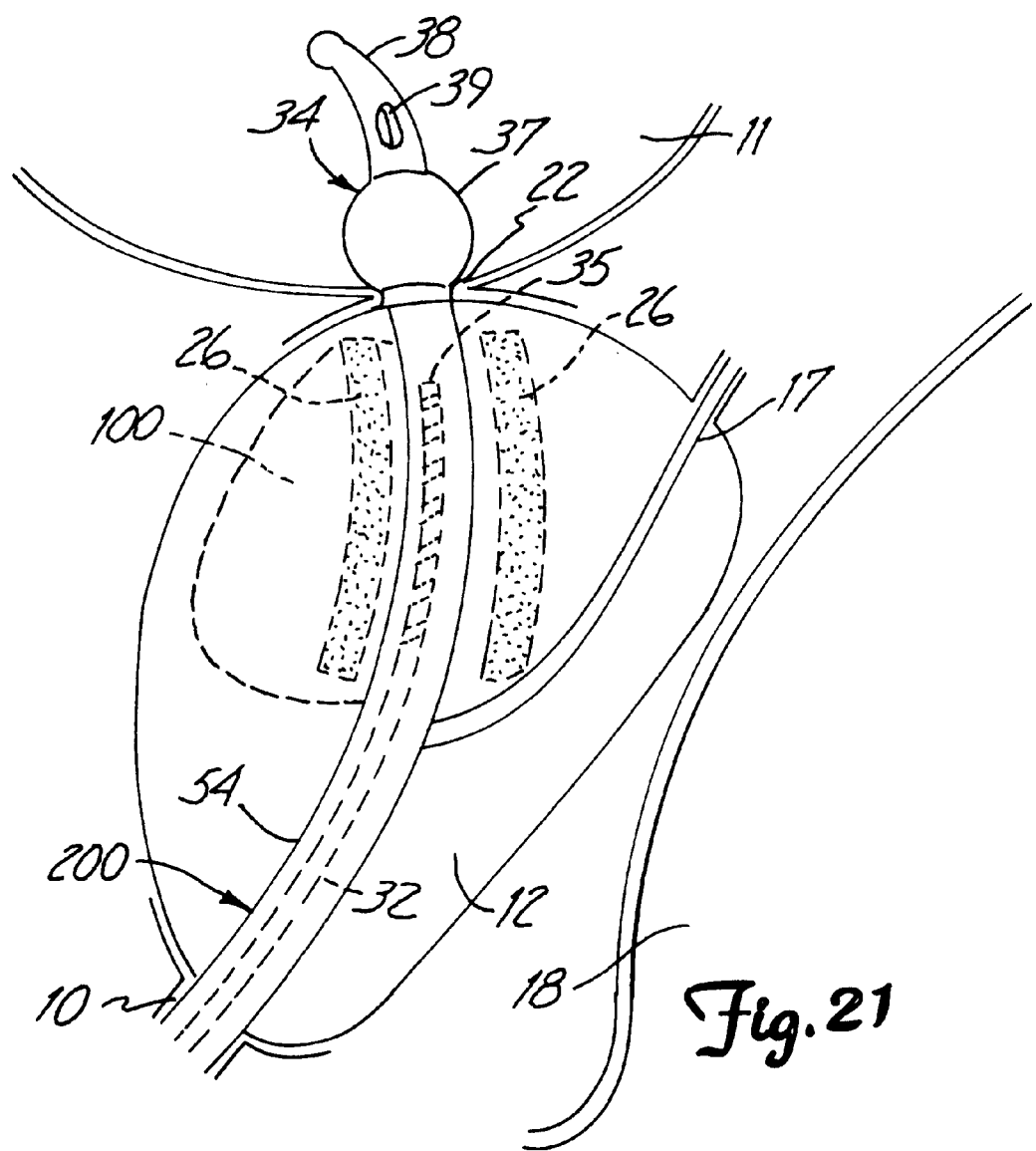

6,123,083

DEVICE AND METHOD FOR TREATMENT OF A PROSTATE WHILE PREVENTING URETHRAL CONSTRICTION DUE TO COLLAGEN RICH TISSUE SHRINKAGE

BACKGROUND OF THE INVENTION

The present invention relates to the field of microwave thermal therapy of tissue. In particular, the present invention relates to a catheter for microwave thermal and cooling therapy of tissue adjacent a urethra to attain a selected width of at least a portion of the lower urinary tract during thermal therapy of prostatic tissue.

Many conduits are used in the human body to pass substances such as gases, fluids or solids from one organ to another organ, or out of the body. From time to time, some bodily conduits become restricted due to an obstruction, or restricted from another tissue impinging on the conduit. With such an obstruction or impingement, the conduit can lose its ability to pass fluids and/or other substances.

One example of a conduit that becomes restricted is the urethra, which is a portion of the lower urinary tract passing through the prostate. The prostate gland encircles the urethra immediately below the bladder. The prostate, which is the most frequently diseased of all internal organs, is the site of a common affliction among older men, benign prostatic hyperplasia (BPH), as well as a more serious affliction, cancer. BPH is a nonmalignant, bilateral nodular tumorous expansion of prostate tissue occurring mainly in the transition zone of the prostate. Left untreated, BPH causes obstruction of the urethra which usually results in increased urinary frequency, urgency, incontinence, nocturia and slow or interrupted urinary stream.

Recent treatment of BPH includes transurethral microwave thermal therapy in which microwave energy is employed to elevate the temperature of tissue surrounding the prostatic urethra above about 45° C., thereby thermally damaging the tumorous prostate tissue. Despite recent successes in ablating such tumorous tissue by transurethral thermal therapy, further improvements can be made in this therapy to further maintain or enhance the patency of the lower urinary tract after the thermal therapy treatment. Maintaining or enhancing the patency of the lower urinary tract will improve functions such as urine flow which are not always improved with transurethral thermal therapy treatment (despite ablation of the tumorous tissue causing constriction of the urethra), and is accordingly highly desirable.

SUMMARY OF THE INVENTION

The present invention is a method for thermally treating tissue adjacent a bodily conduit, such as a urethra, while preventing restrictions of the bodily conduit due to heat-induced shrinkage of collagen rich tissue surrounding the bodily conduit. A select volume of collagen-containing tissue surrounding the urethra is heated to a temperature above about 45° C. for time sufficient to substantially destroy the select volume of tissue and above a predetermined collagen transition temperature (e.g. about 60° C.) for time sufficient to cause the collagen-containing prostatic tissue to be capable of being plastically remodeled. A selected shape of the urethra is defined while maintaining the select volume of tissue above the predetermined collagen transition temperature for a time sufficient to permit the tissue to assume the selected shape. The select volume of tissue is then allowed to cool to a temperature below the collagen transition temperature while continuing to define the selected shape of the urethra for a time sufficient to cause plastic remodeling of the tissue.

Alternatively, a diameter of the urethra may be preserved by preventing collagen rich tissue surrounding the urethra from being heated to a temperature above the collagen transition temperature. An energy emitting element of a probe positioned in the urethra is energized sufficiently to heat the tissue adjacent the urethra to temperatures of at least 45° C. but less than the predetermined collagen transition temperature. This heating regimen permits ablation of tumorous tissue adjacent the urethra while avoiding narrowing of the urethra due to heat-induced shrinkage of collagen rich tissue surrounding the urethra.

BRIEF DESCRIPTION OF THE DRAWINGS

FIG. 4 is a plan view of the urethral catheter of the present invention.

FIG. 7 is a perspective view of a combined tip, retention balloon, and cooling balloon of the urethral catheter of the present invention.

FIG. 8 is an enlarged sectional view of the proximal end of the urethral catheter of the present invention.

FIG. 15 is a plan view of an alternate embodiment of the urethral catheter of the present invention.

FIG. 16 is a cross-sectional view of the urethral catheter of FIG. 15 taken along line 16—16.

FIG. 17 is an enlarged sectional view of the proximal end of the urethral catheter of the present invention of FIG. 16 taken along line 17—17.

FIG. 18 is a plan view of an alternate embodiment of the urethral catheter of the present invention.

FIG. 19 is a cross-sectional view of the urethral catheter of FIG. 18 taken along line 19—19.

FIG. 20 is a cross-sectional view of the urethral catheter of FIG. 18 taken along line 20—20.

FIG. 21 is a vertical sectional view of a urethra shown with a catheter of FIG. 18 of the present invention positioned therein.

DETAILED DESCRIPTION OF THE PREFERRED EMBODIMENTS

The method of the present invention permits thermal therapy of tumorous tissue adjacent a urethra while preventing restrictions of the urethra due to heat-induced shrinkage of collagen rich tissue surrounding the urethra. Examples and alternatives of the method of the present invention will be described and illustrated below after a brief discussion of collagen.

Collagen is a principal component of connective tissue and fibromuscular tissues. Collagen also has known properties such as plastic remodeling (e.g. irreversible shrinkage) when subjected to high temperatures (e.g. about 60° C. to 70° C.). Specific remodeling temperatures are generally more exactly identifiable for a type and age of tissue in a particular location of the body. General principles of collagen and collagen reactivity to thermal treatment are known in the art and are described in the following articles, amongst others: Gustavson, *The Chemistry and Reactivity of Collagen*, Academic Press, Inc., New York, 1956, specifically including p.p. 211–220; Agah et. al., *Rate Process Model For Arferial Tissue Thermal Damage: Implications on Vessel Photocoagulation*, Lasers in Surgery and Medicine, 15:176–184 (1994); Trembly et. al., *Combined Microwave Heating and Surface Cooling of the Cornea*, IEEE Transactions On Biomedical Engineering, Vol. 38, No. 1, 1991, Stringer et. al., *Shrinkage Temperature of Eye Collagen*, Nature, No. 4965, pp. 1307.

Of specific interest, collagen is found in fibromuscular tissue and other interstitial connective tissue forming part of or surrounding various ducts in the body. For example, the urethra is a duct in the lower urinary tract that passes fluid from the bladder, through the prostate, and out of the body via the penis. Proximal portions of the prostatic urethra are surrounded by a ring of fibromuscular tissue and by interstitial tissue in the prostate, both types of tissue including collagen. Manipulation of this collagen in the method of the present invention is used to remedy various dysfunctions of the prostate and/or urethra, such as benign prostatic hyperplasia. Accordingly, the urethra is one example of a duct in the body having collagen rich surrounding tissue and a diameter that must be carefully controlled to maintain normal function, which is addressed by the method of the present invention.

Figure 1:
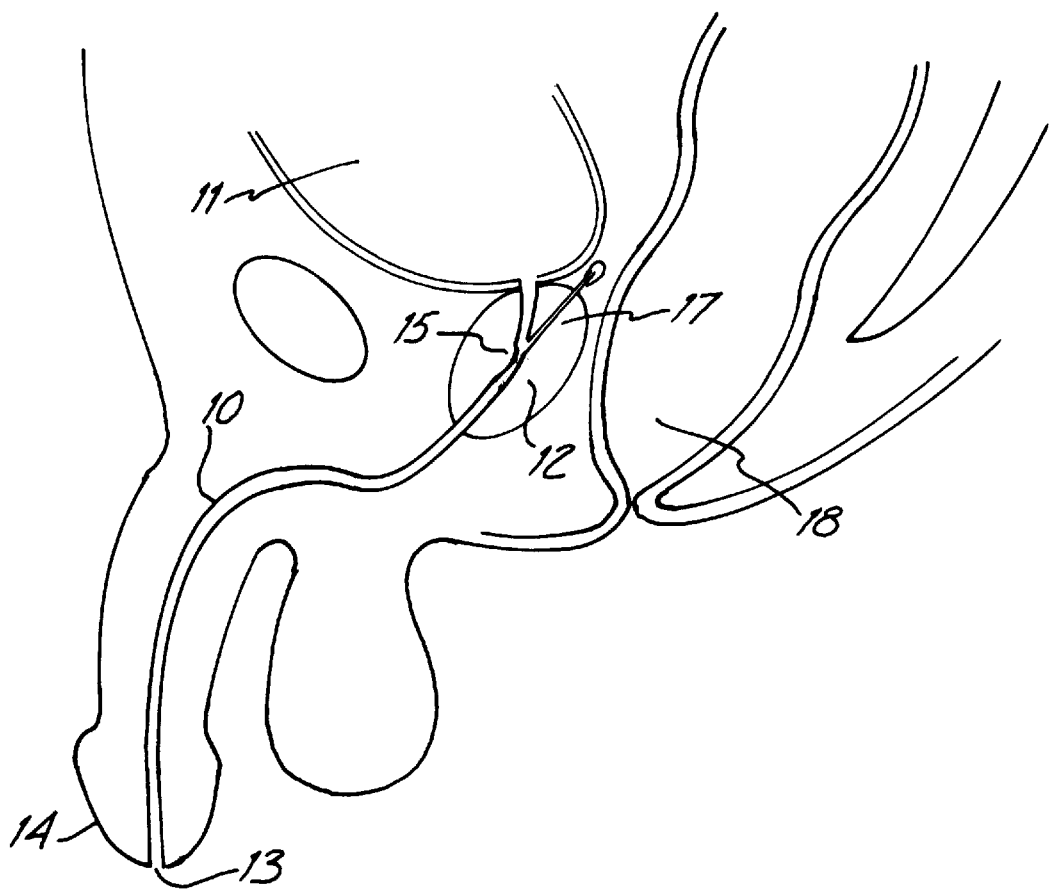
FIG. 1 is a vertical sectional view of a male pelvic region showing the urinary organs affected by benign prostatic hyperplasia.

A first method of maintaining or expanding the diameter of the urethra into a selected urethral shape after microwave thermal therapy treatment for benign prostatic hyperplasia to restore patency to the urethra is illustrated in FIGS. 1–12. FIG. 1 is a vertical sectional view of a male pelvic region showing the effect of benign prostatic hyperplasia (BPH) on the urinary organs. Urethra 10 is a duct leading from bladder 11, through prostate 12 and out orifice 13 of penis end 14. Benign tumorous tissue growth within prostate 12 around urethra 10 causes constriction 15 of urethra 10, which interrupts the flow of urine from bladder 11 to orifice 13. The tumorous tissue of prostate 12 which encroaches urethra 10 and causes constriction 15 can be effectively removed by heating and necrosing the encroaching tumorous tissue. Ideally, with the present invention, periurethral tumorous tissue of prostate 12 anterior and lateral to urethra 10 is heated and necrosed while avoiding unnecessary and undesirous damage to urethra 10 and to adjacent healthy tissues, such as ejaculatory duct 17 and rectum 18. A selective heating of benign tumorous tissue of prostate 12 (transurethral thermal therapy) is made possible by a microwave antenna-containing catheter of the present invention, shown later in FIGS. 4–12.

Figure 2:
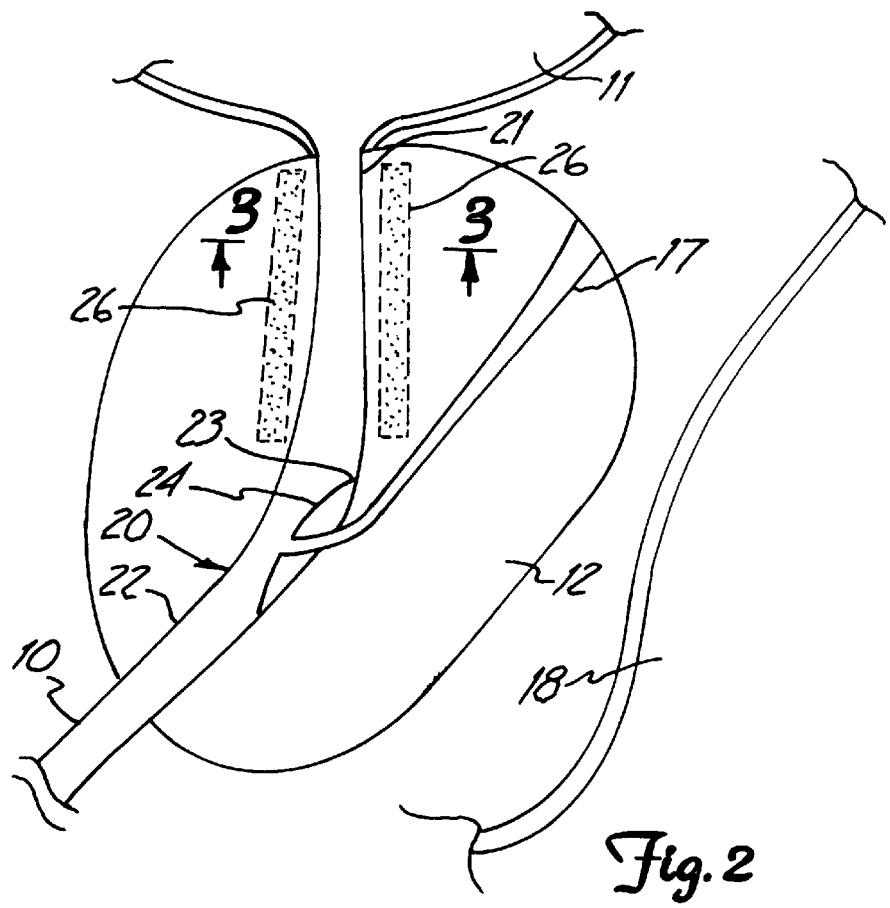
FIG. 2 is a vertical sectional view of a urethra extending through a prostate.

FIG. 2 is a sectional view of prostate 12 illustrating specific anatomical features of urethra 10 in prostate 12. Prostatic urethra 20 includes proximal segment 21, distal segment 22, point of angulation 23, and verumontanum 24. Proximal segment 21 extends from point 23 to bladder 11 while distal segment 22 extends from point 23 to the remaining distal portion of prostate 12. Verumontanum 24 is located in distal segment 22 of prostatic urethra 20 adjacent to and just distal to point of angulation 23. Ejaculatory duct 17 extends through verumontanum 24 and is exposed in distal segment 22 of prostatic urethra 20.

Tissue 26 surrounds proximal segment 21 of prostatic urethra 20 and defines a ring of tissue about urethra 10 that is rich in collagen. Tissue 26 is closely adjacent to prostatic urethra 20 and includes a ring of fibromuscular tissue and interstitial tissue that includes collagen. Tissue 26 is situated amidst tumorous tissue in prostate 12 (particularly in the transition zone of the prostate) that comprises BPH and which causes a constriction 15 of urethra as shown in FIG. 1.

Figure 3:
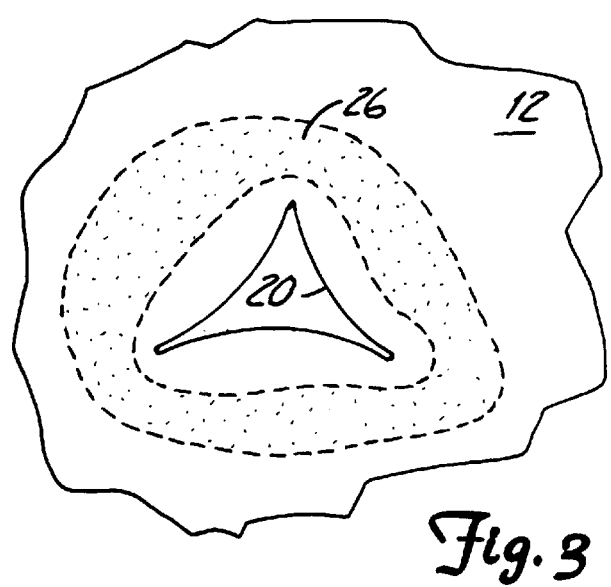
FIG. 3 is a sectional view of a urethra of FIG. 2 as seen along the lines 3—3.

FIG. 3 is a cross-sectional view of prostatic urethra 20 taken along line 3—3 of FIG. 2. FIG. 3 further illustrates prostatic urethra 20 to show its generally triangular shaped transverse cross-section and to show the ring of the collagen rich tissue 26 surrounding the prostatic urethra 20. Prostatic urethra 20 expands when fluid (e.g. urine) passes through the urethra unless BPH or other disease process in the prostate constricts the urethra.

Heating of tissue 26 above a predetermined collagen transition temperature (e.g. 60° C. to 70° C.) during a microwave thermal therapy treatment to treat BPH can potentially cause tissue 26 to shrink about urethra 10 causing a constriction of prostatic urethra 20. Since the objective of thermal therapy is to alleviate constrictions of the urethra, such shrinking of the urethra would be undesirable. The method of the present invention of maintaining an unobstructed shape of the urethra is employed to prevent the potential constriction of the urethra due to thermal collagen shrinkage while permitting a microwave thermal therapy treatment to eliminate constriction 15 caused by BPH.

A microwave antenna-containing catheter 29 employed in the method of the present invention, shown in FIGS. 4–12, includes a dilation and cooling balloon adapted for dilating and cooling tissue surrounding the urethra. As shown in FIG. 4, catheter 29 generally includes multi-port manifold 30, multi-lumen shaft 32, tip 34, and microwave antenna 35 (or some other suitable energy emitting element). Tip 34 includes dilation and cooling balloon 36, retention balloon 37, tip portion 38, and side port 39 for communication with a urine drainage lumen. Manifold 30 includes inflation port 40, urine drainage port 42, microwave antenna port 44, cooling fluid intake port 46, and cooling fluid exhaust port 48. Ports 40–48 of manifold 30 communicate with corresponding lumens within shaft 32. Catheter 29 is employed in a thermal therapy catheter system further including a cooling system, a microwave generating source, and a urethral thermometry unit. These additional elements of a thermal therapy catheter system are disclosed in Rudie et al. U.S. Pat. No. 5,413,588, assigned to Urologix, Inc., which is hereby incorporated by reference.

Catheter shaft 32 includes distal end 50, proximal end 52, and outer surface 53 having first side 54 and second side 55. When catheter 29 is placed within a urethra, first side 54 is oriented anteriorly and second side 55 is oriented posteriorly toward rectum 18 (shown in FIG. 1). Shaft 32 is connected to manifold 30 at shaft distal end 50 and is long enough to permit insertion of retention balloon 37 through urethra 10 and into bladder 11. Manifold 30 and multi-lumen shaft 32 are preferably extruded of medical-grade silicone sold by Dow Corning under the trademark Silastic® type Q7-4850, and type Q7-4780, respectively. Alternative materials can include a polystyrene material sold by Advanced Elastomer Systems, L.P. under the trademark Santoprene®. The material of manifold 30 and shaft 32 preferably has a Shore D hardness between 50D and 80D. Catheter shaft 32 can also include several radiopaque markers disposed adjacent proximal end 52 adjacent dilation and cooling balloon 36 to facilitate positioning of catheter 29 within prostatic urethra 20 via fluoroscopy.

Dilation and cooling balloon 36 is positioned adjacent proximal end 52 of catheter shaft 32 alongside microwave antenna 35, which extends within shaft 32. Dilation and cooling balloon 36 is provided so that, when filled with a cooling fluid, dilation and cooling balloon 36 prevents unwanted heating of the prostatic urethra 20 adjacent catheter shaft 32 during thermal therapy. In addition, inflation of dilation and cooling balloon 36 applies outward radial force to the urethral wall and thereby provides an inner boundary surface to prostatic urethra 20 while microwave energy radiating from microwave antenna 35 heats tumorous prostatic tissue (perhaps including some or all of tissue 26 surrounding catheter 29) above a collagen transition temperature. This dilation force prevents the collagen rich surrounding tissue 26 from shrinking about prostatic urethra 20 once tissue 26 is heated above the collagen transition temperature. Cooling of tissue 26 with dilation and cooling balloon 36 is maintained after the heating step until surrounding tissue 26 cools to a temperature below the collagen transition temperature. This step causes collagen rich surrounding tissue 26 to remain plastically modeled in a shape determined by the inflated shape of balloon 36 without shrinking around and impinging prostatic urethra 20.

Alternatively, dilation and cooling balloon 36 may be used according to a second method of the present invention to prevent heating of collagen rich surrounding tissue 26 above the collagen transition temperature. The pressure, temperature, time, power and other parameters involving the circulation of cooling fluid through balloon 36 and/or the application of power to antenna 35 may be adjusted to ensure that the temperature of tissue 26 surrounding prostatic urethra 20 remains below the collagen transition temperature (e.g. about 60° C.) while permitting heating of a targeted volume of tumorous tissue above about 45° C. for a period of time sufficient to substantially destroy the tumorous tissue. In this embodiment, balloon 36 need not exert outward radial force sufficient to provide an inner boundary to prostatic urethra 20, since collagen rich surrounding tissue 26 is not heated above the collagen transition temperature and therefore will not shrink to constrict the urethra.

Figure 5:
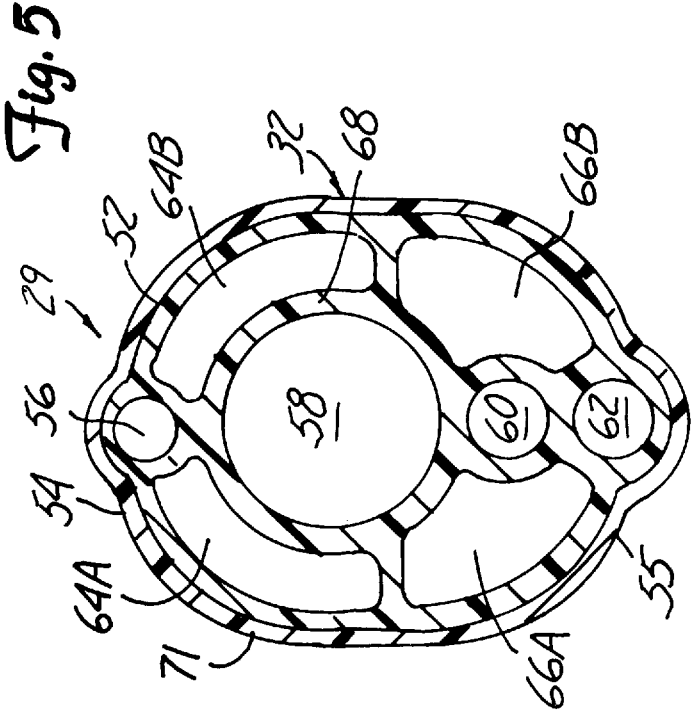
FIG. 5 is a cross-sectional view of the urethral catheter of FIG. 4 taken along line 5—5.

Dilation and cooling balloon 36 operates in conjunction with multi-lumen shaft 32. As shown in FIG. 5, multi-lumen shaft 32 includes temperature sensing lumen 56, microwave antenna lumen 58, urine drainage lumen 60, retention balloon inflation lumen 62, cooling fluid intake lumens 64A and 64B, and cooling fluid exhaust lumens 66A and 66B. The multi-lumen shaft 32 is fully described in detail in U.S. Pat. No. 5,628,770, issued May 13, 1997 and assigned to Urologix, Inc., entitled DEVICE FOR TRANSURETHRAL THERMAL THERAPY, which is hereby incorporated by reference.

Temperature sensing lumen 56 is positioned near first side 54 of shaft 32 and is configured to permit insertion of a thermometry sensor within shaft 32 to monitor the temperature adjacent to first side 54 when shaft 32 is inserted within urethra 10.

Microwave antenna lumen 58 is positioned eccentric to the longitudinal axis of catheter shaft 32, antenna lumen 58 being positioned nearer shaft first side 54 than shaft second side 55. Microwave antenna lumen 58 is adapted for receiving microwave antenna 35 to be permanently positioned within antenna lumen 58 of shaft 32 near dilation and cooling balloon 36 (FIG. 4) so that antenna 35 will be generally situated adjacent to prostate 12 (including surrounding tissue 26) when shaft 32 is properly positioned within urethra 10. A microwave antenna suitable for incorporation into catheter 29 of the present invention is disclosed in Rudie et al. U.S. Pat. No. 5,413,588, issued May 9, 1995, which has been incorporated herein by reference.

Urine drainage lumen 60 is positioned adjacent antenna lumen 58 between antenna lumen 58 and shaft second side 55. Urine drainage lumen 60 communicates with urine drainage port 42 of manifold 30 at distal shaft end 50 and with side port 39 of tip 34 at proximal shaft end 52 to define a drainage path for urine when tip 34 of catheter 29 is inserted within bladder 11. Retention balloon inflation lumen 62 is positioned near second side 55 of shaft 32, generally between urine drainage lumen 60 and second side 55. Retention balloon inflation lumen 62 communicates with inflation port 40 of manifold 30 to permit inflation and deflation of retention balloon 37.

As shown in FIG. 5, multi-lumen catheter shaft 32 also includes cooling fluid intake lumens 64A, 64B and cooling fluid exhaust lumens 66A, 66B. Cooling lumens 64A–66B surround antenna lumen 58, so that when filled with a cooling fluid, heat energy generated by microwave energy is conducted away from tissues immediately surrounding catheter shaft 32 via thermal conduction and microwave energy emitted by microwave antenna 35 is selectively absorbed.

Cooling fluid intake lumens 64A, 64B are positioned adjacent to shaft first side 54, between first side 54 and antenna lumen 58 while cooling fluid exhaust lumens 66A, 66B are positioned adjacent to shaft second side 55 between second side 55 and antenna lumen 58. Both cooling fluid intake lumens 64A, 64B, and cooling fluid exhaust lumens 66A, 66B extend from shaft distal end 50 to shaft proximal end 52 where each of the lumens 64A,64B,66A,66B terminate. Cooling fluid intake lumens 64A, 64B and cooling fluid exhaust lumens 66A, 66B preferably have a generally arc-shaped transverse cross-section configured to partially surround antenna lumen 58. In combination, cooling lumens 64A, 64B and cooling lumens 66A, 66B substantially surround antenna lumen 58 about a substantial majority (about 75%) of a circumference of antenna lumen 58. Cooling lumens 64A, 64B and 66A, 66B are defined by single wall 68 and preferably have a wall thickness of 0.009 inches. The cooling exhaust lumens 66A, 66B preferably have a radial thickness greater than a radial thickness of the cooling intake lumens 64A, 64B. For example, the cooling intake lumens 64A, 64B preferably have a radial thickness of 0.028 inches and the cooling exhaust lumens 66A, 66B preferably have a radial thickness from about 0.28 inches (adjacent cooling intake lumens 64A,64B) to about 0.037 inches (adjacent urine drainage lumen 60).

Figure 6:
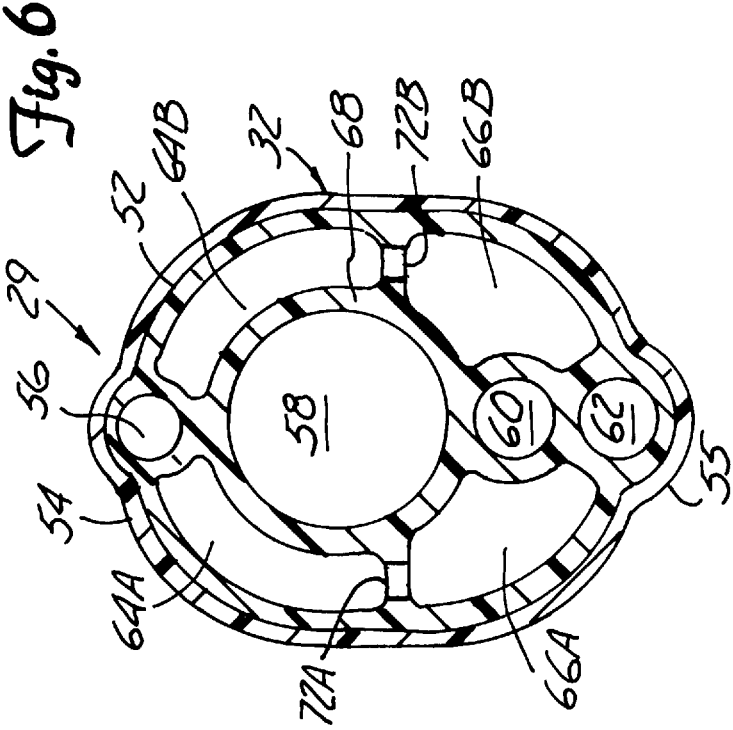
FIG. 6 is a cross-sectional view of the urethral catheter of FIG. 4 taken along line 6—6.

As shown in FIG. 6, cooling fluid intake lumens 64A and 64B are in communication with cooling exhaust lumens 66A and 66B, respectively, near proximal shaft end 52 of catheter shaft 32 adjacent retention balloon 37 (FIG. 4). In particular, hole 72A defined in wall 68 between cooling intake lumen 64A and cooling exhaust lumen 66A permits communication between the respective lumens 64A and 66A. Similarly, hole 72B defined in wall 68 between cooling intake lumen 64B and cooling exhaust lumen 66B permits communication between the respective lumens 64B and 66B. Lumens 56–66B, except for urine drainage lumen 60, are all sealed shut proximal to holes 72A, 72B.

Cooling intake lumens 64A and 64B and cooling exhaust lumens 66A and 66B cooperate with a cooling system (not shown) via ports 44 and 46 of manifold 30 to provide a selectively controlled flow of fluid through cooling lumens 64A, 64B, 66A, and 66B during a treatment session. Cooling fluid circulating through cooling lumens 64A–66B carries heat away from tissues (e.g. prostatic urethra 20) immediately surrounding catheter shaft 32 and selectively absorbs microwave energy radiating from microwave antenna 35. In one embodiment, intake lumens 64A, 64B and exhaust lumens 66A, 66B are supplied with cooling fluid from a cooling system via manifold 30, such as water, for example, or some other suitable cooling fluid. Cooling fluid from the cooling system is chilled and pumped through cooling fluid intake lumens 64A, 64B toward proximal shaft end 52. Under fluid pressure, the cooling fluid enters cooling fluid exhaust lumens 66A, 66B through holes 72A, 72B and returns to the cooling system through exhaust lumens 66A, 66B for re-chilling and re-circulation.

Dilation and cooling balloon 36 comprises a portion of tip 34, which is secured onto proximal end 52 of shaft 32. As shown in FIG. 7, tip 34 comprises a single member including dilation and cooling balloon 36, transition portion 74, retention balloon 37, and tip portion 38. Retention balloon 37 is a flexible tubular portion while tip portion 38 comprises a flexible curved body. Dilation and cooling balloon 36 is located just distally from retention balloon 37 and is minimally spaced from retention balloon 37 so that dilation and cooling balloon 36 generally lies adjacent to prostate 12 and preferably extends longitudinally into a region of the neck of bladder 11 when retention balloon 37 is inflated within bladder 11. Dilation and cooling balloon 36 is a flexible tubular member that includes proximal end 80, expandable portion 82 and distal end 86. Expandable portion 82 can be inflated and deflated (shown in FIG. 7) with sufficient pressure to dilate surrounding tissue 26 (FIGS. 2 and 3) to attain a selected shape of prostatic urethra 20 by the selective introduction and removal of an inflation fluid within an interior of expandable wall portion 82.

Tip portion 38 and retention balloon 37 of tip 34 are formed by liquid injection molding from a flexible, medical-grade silicone sold by Dow Corning under the trademark Silastic® Q-7-4720, or a similar material such as a thermoplastic elastomer sold under the trademark Santoprene®, Kraton® or Pebax®. The silicone preferably has a material hardness of 20 Shore A, which is relatively soft to provide an atraumatic tip. Tip 34 can also include a radiopaque filler such as barium sulfate added to the silicone material to make tip 34 observable under fluoroscopy.

Dilation and cooling balloon 36 is preferably made of cross-linked polyethylene or polyethylene terephalate, or some other supple, resilient material capable of permitting low compliant expansion (under inflation pressure) sufficient to dilate the urethra and surrounding tissue. Dilation and cooling balloon 36 is connected directly to shaft 32 and is also preferably connected to retention balloon 37 via transition portion 74 using techniques known to those in the art.

FIG. 8 provides a more detailed view of dilation and cooling balloon 36 and catheter shaft 32 at proximal shaft end 52. Dilation and cooling balloon 36 surrounds catheter shaft 32 adjacent microwave antenna 35. Proximal end 80 further defines proximal waist 81 for securing dilation and cooling balloon 36 onto shaft 32 and is positioned adjacent transition portion 74 proximal to antenna 35. Distal end 86 further defines distal waist 87 for securing dilation and cooling balloon 36 onto shaft 32 and is positioned distal to antenna 35.

Dilation and cooling balloon 36 is secured onto proximal shaft end 52 of shaft 32 with an adhesive. Proximal waist 81 of dilation and cooling balloon 36 is adhesively bonded to catheter shaft outer surface 53, and distal waist 87 of dilation and cooling balloon 36 is adhesively bonded to catheter shaft outer surface 53. Proximal waist 81 is also preferably joined to transition portion 74 using techniques known in the art.

Figure 9A:
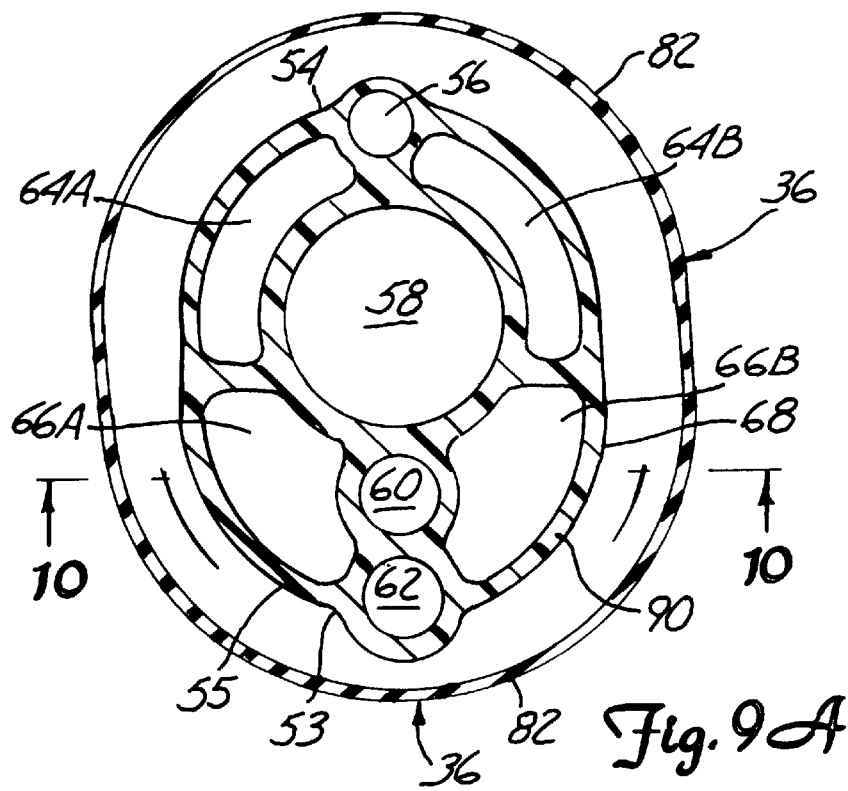
FIG. 9A is a sectional view of the catheter shaft of FIG. 4 taken along lines 9A—9A.
Figure 9B:
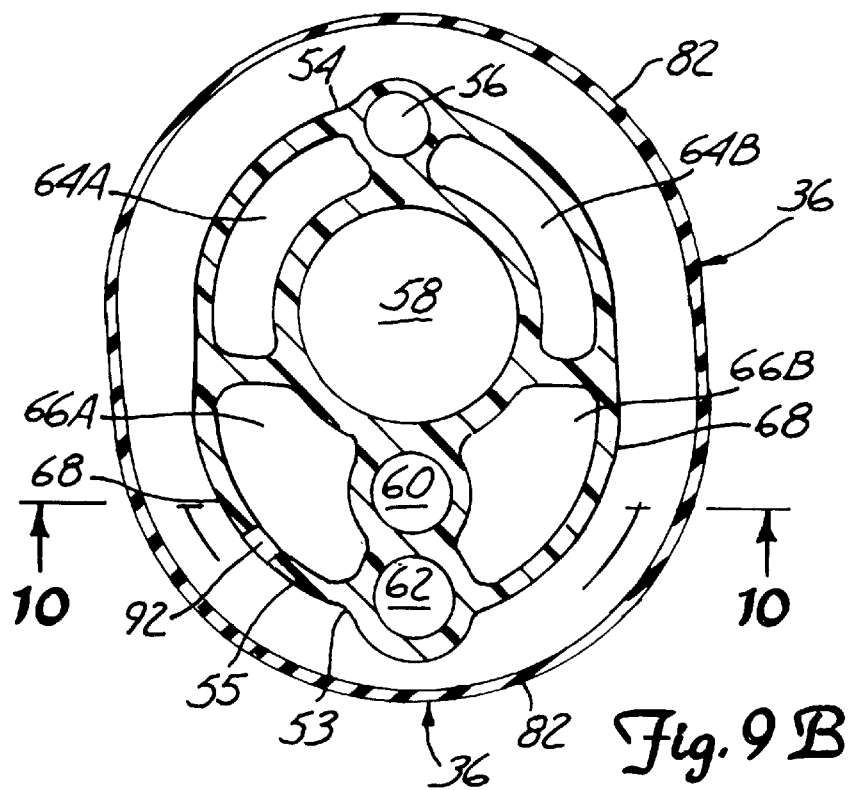
FIG. 9B is a sectional view of the catheter shaft of FIG. 4 taken along lines 9B—9B.

This arrangement creates a sealed connection at distal end 86 and proximal end 80 to secure dilation and cooling balloon 36 on catheter shaft 32. An inner surface 83 of expandable portion 82 is spaced from and is not secured to shaft outer surface 53 so that expandable portion 82 remains free to expand relative to catheter outer surface 53 upon introduction and passage of an inflation cooling fluid (from cooling lumens 66A, 66B as shown in FIGS. 9A and 9B) through an interior of dilation and cooling balloon 36. Expandable portion 82 of dilation and cooling balloon 36 is positioned adjacent to microwave antenna 35 so that in use, cooling fluid circulated under pressure within dilation and cooling balloon 36 is capable of maintaining a selected shape of prostatic urethra 20 and thereby plastically remodeling surrounding tissue 26 accordingly.

As shown in FIG. 8, catheter 29 also includes fiber optic thermometry unit 88 including shaft 87 and sensor 89. At its distal end, thermometry unit shaft 87 extends distally outward through a port (not shown) in manifold 30 and extends proximally through temperature sensing lumen 56 along the length of catheter shaft 32. Thermometry shaft 87 extends into dilation and cooling balloon 36 adjacent antenna 35 via hole 91 in an outer wall of temperature sensing lumen 56. Thermometry unit shaft 87 floats freely within temperature sensing lumen 56 but is secured at its proximal end with adhesive along inner surface 83 of expandable wall portion 82 of dilation and cooling balloon 36. This arrangement places thermometry sensor 89 closely adjacent to prostatic urethra 20 to facilitate accurate temperature measurements of the urethra 10.

As also shown in FIG. 8, dilation and cooling balloon 36 extends for a length adjacent proximal shaft end 52 that is substantially less than the length of catheter shaft 32, yet equal to or greater than a length of microwave antenna 35. For example, to accommodate different size prostates, dilation and cooling balloon 36 has a length of about 1.0 to 4.0 centimeters with expandable portion 82 having a length of about 1.0 to 3.5 centimeters. In a preferred embodiment, dilation and cooling balloon 36 has a length of about 3.0 centimeters and expandable portion 82 has a length of about 2.5 centimeters.

Dilation and cooling balloon 36 is further shown in cross section in FIGS. 9A–9B, which are cross-sectional views of shaft 32 taken along lines 9A—9A and 9B—9B in FIG. 4. FIGS. 9A and 9B illustrate the manner in which dilation and cooling balloon 36 communicates with cooling lumens 66A, 66B. Expandable portion 82 of dilation and cooling balloon 36 surrounds shaft outer surface 53 including cooling fluid intake and exhaust lumens 66A, 66B. Dilation and cooling balloon 36 preferably has a wall thickness of about 0.0005 to 0.005 inches. The chamber defined between catheter outer surface 53 and expandable portion 82 of dilation and cooling balloon 36 typically has a radial thickness of about 0.5 to 5.0 millimeters.

Figure 10:
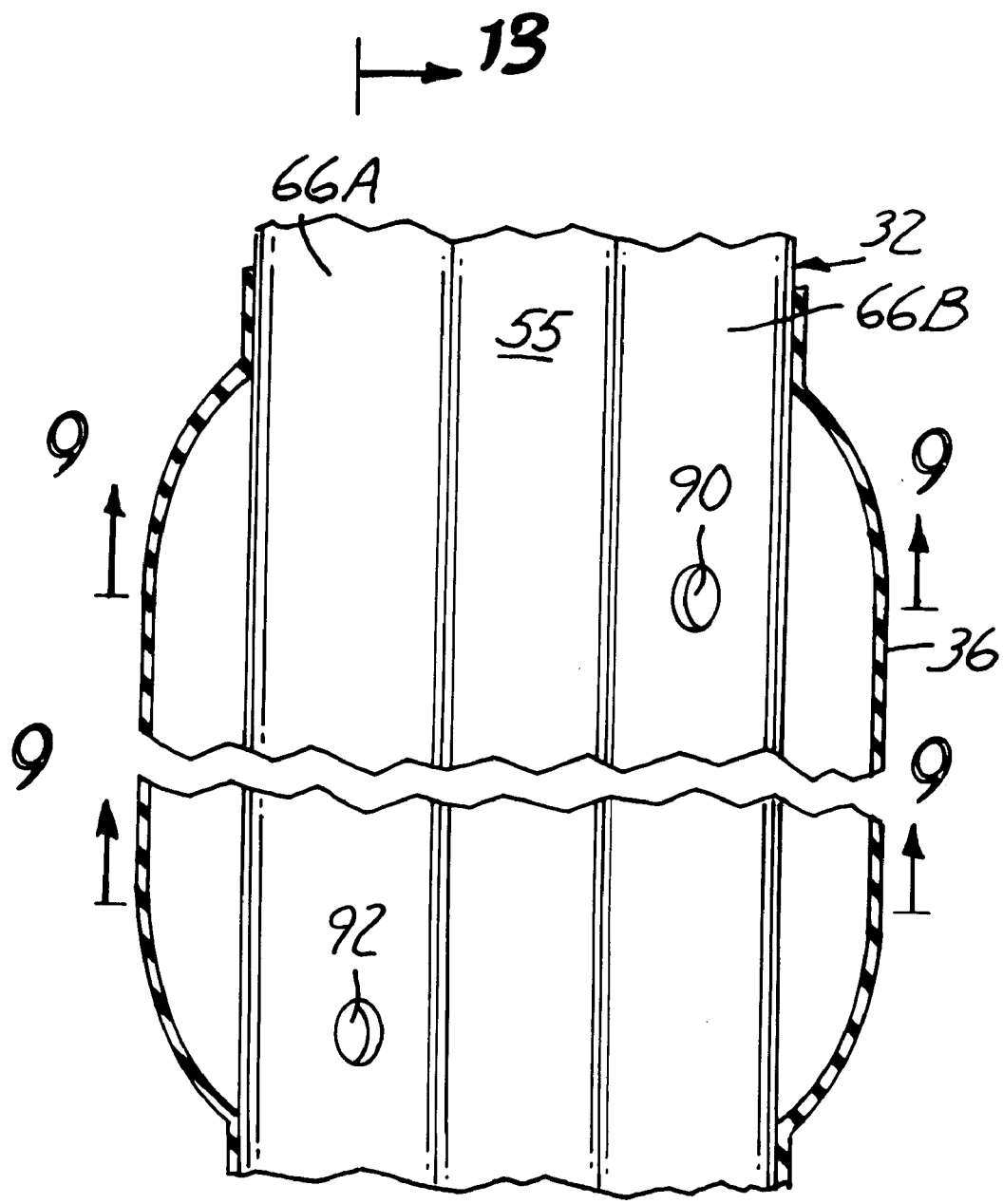
FIG. 10 is a plan view of a second side of the catheter shaft shown in FIGS. 9A and 9B with a balloon portion removed and as taken along lines 10—10.

As shown in FIG. 9A, side wall 68 of catheter shaft 32 defines exhaust lumen 66B including hole 90 and as shown in FIG. 9B, defines exhaust lumen 66A including hole 92. Hole 90 permits communication between cooling exhaust lumen 66B and an interior of dilation and cooling balloon 36 and hole 92 permits communication between an interior of dilation and cooling balloon 36 and exhaust lumen 66A. Since fluid within cooling lumens 66A and 66B is flowing under pressure distally along catheter shaft 32, fluid within lumen 66B enters inflatable dilation and cooling balloon 36, passes through dilation and cooling balloon 36 and exits into exhaust lumen 66A to recirculate through a cooling system via manifold 30. As shown in FIG. 10, holes 90 and 92 are axially spaced apart and are laterally spaced apart. This arrangement creates a pressure differential between the respective holes 90 and 92 causing dynamic inflation of the dilation and cooling balloon 36 and insuring that adequate fluid circulation will occur through dilation and cooling balloon 36 as cooling fluid moves through cooling lumens 64A, 64B and 66A, 66B. The rate of cooling fluid intake into lumens 64A, 64B or the rate of cooling fluid exhaust out of lumens 66A, 66B can be manipulated by a cooling system via manifold 30 to selectively modify the fluid pressure gradient between hole 90 and hole 92 to maintain dilation and cooling balloon 36 in an inflated state and to ensure a constant flow of cooling fluid therethrough.

Additional holes can be formed in the side walls of cooling intake lumens 64A, 64B as necessary, in combination with holes (e.g., 90 and 92) in cooling exhaust lumens 66A, 66B to achieve the desired level of pressurization and recirculation. Moreover, the relative sizing of holes 90 and 92, respectively, also can be modified to control the flow of cooling fluid in and out of the dilation and cooling balloon 36. For example, hole 90 can be made larger than hole 92 to accentuate filling of dilation and cooling balloon 36. Finally, if necessary, a pressurization and cooling recirculation pump system is incorporated into the cooling system to insure that dilation and cooling balloon 36 is inflated with a pressure sufficient to dilate surrounding tissue and sufficient to insure adequate cooling of prostatic urethra 20 by circulation of cooling fluid passing into, through, and out of dilation and cooling balloon 36 via cooling lumens 64A–66B.

Figure 11:
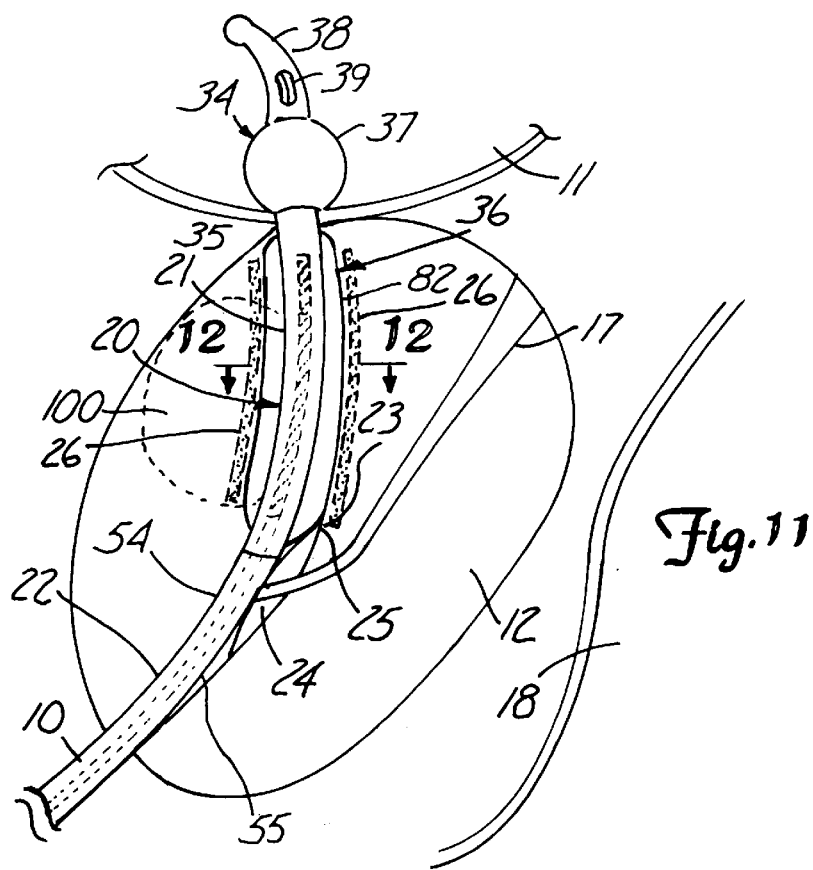
FIG. 11 is a vertical sectional view of a urethra of FIG. 2 shown with a catheter of the present invention positioned therein.

FIG. 11 shows an enlarged view of the male pelvic region of FIG. 1 with catheter 29 properly positioned for use within urethra 10. Catheter 29 is inserted into and through urethra 10 using techniques known to those skilled in the art until tip 34 is positioned in bladder 11. Retention balloon 37 is then inflated via inflation lumen 62 to secure balloon 37 in bladder 11, thereby positioning catheter shaft 32 within prostatic urethra 20 so that antenna 35 is adjacent tumorous tissue 100. In this position, tissue 26 surrounds prostatic urethra 20 and surrounds dilation and cooling balloon 36 of catheter 29, and dilation and cooling balloon 36 is minimally spaced from balloon 37 so that dilation and cooling balloon 36 preferably extends longitudinally into a region of the neck of bladder 11.

With catheter 29 in this position, a method of ablating tumorous prostatic tissue while preventing collagen shrinkage of surrounding tissue 26 includes the following steps. Antenna 35 is energized with a microwave energy generating source (connected via manifold 30) to cause microwave radiation to be emitted radially from antenna 35 into tissue 26 the targeted prostatic tissue (e.g., 100) including tissue 26 surrounding antenna 35. The microwave radiation is applied at frequencies of 902–928 MHZ and at a power and for a time sufficient to inductively heat and substantially destroy tumorous prostatic tissue. The tumorous tissue is heated according to a time and temperature relationship to achieve heating of targeted tissue above 45° C. which substantially destroys the tumorous tissue.

In order to preserve the urethral wall, a cooling system is operated during heating to provide a continuous flow of cooling fluid (via manifold 30) through cooling fluid intake lumens 64A, 64B, cooling fluid exhaust lumens 66A, 66B, and dilation and cooling balloon 36. Dilation and cooling balloon 36, which is shown in FIG. 11 in an inflated state, is inflated by the introduction and continuous circulation of fluid through dilation and cooling balloon 36 via holes 90 and 92 (see FIGS. 9A, 9B, and 10). Cooling fluid circulating through dilation and cooling balloon 36 cools prostatic urethra 20 to preserve urethra 10 during the heating step of the thermal therapy treatment. Circulation of the cooling fluid through dilation and cooling balloon 36 may be controlled to prevent surrounding tissue 26 from being heated to a temperature above a collagen transition temperature (e.g. about 60° C.), according to a second method of the present invention. By maintaining the temperature of surrounding tissue 26 below the collagen transition temperature, potential constriction of prostatic urethra 20 due to collagen shrinkage is avoided.

Figure 12:
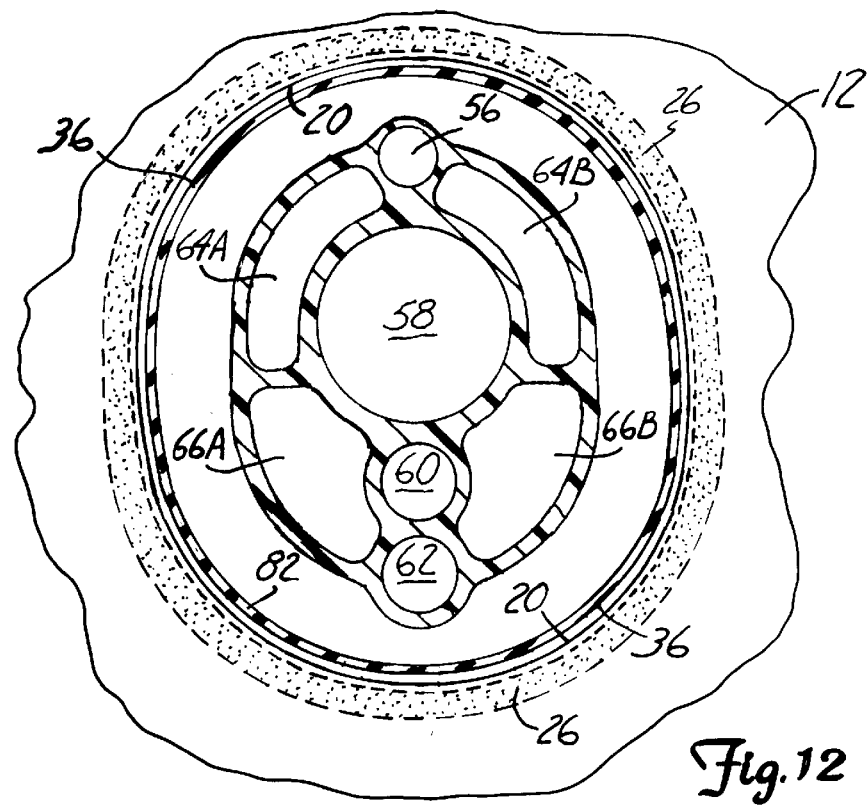
FIG. 12 is a sectional view of a urethra of FIG. 11 as seen along the lines 12—12 with a catheter of the present invention positioned therein.

FIG. 12 shows a transverse cross sectional view of FIG. 11 taken along lines 12—12 to further illustrate the relative position of dilation and cooling balloon 36, prostatic urethra 20, and surrounding tissue 26. Upon inflation of dilation and cooling balloon 36, expandable portion 82 of dilation and cooling balloon 36 conforms to the inner diameter of prostatic urethra 20 and surrounding tissue 26, contacting the urethral wall.

A discussion on the time and temperature relationship for causing necrosis of tissues is presented in the literature known to those skilled in the art including, but not limited to: Henriques, Studies of Thermal Injury, V. The Predictability and Significance of Thermally Induced Rate Processes Leading To Irreversible Epidermal Injury, ARCHIVES OF PATHOLOGY, Volume 43, pp. 489–502 (1947) and related articles by Henriques; and Dickson et. al., Thermosensitivity of Neoplastic Tissues In Vivo, HYPERTHERMIA IN CANCER THERAPY, Chapter 5, including supporting articles cited therein.

Cooling fluid exhaust lumens 66A, 66B absorb more microwave energy than cooling fluid intake lumens 64A, 64B so that the intensity of the electromagnetic energy delivered by antenna 35 is greater on catheter first side 54 than on catheter second side 55. As a result, a relatively large volume of tissue enveloping the tumorous prostatic tissue within zone 100 adjacent catheter first side 54 is heated according to a time and temperature relationship sufficient to effectively necrose the tumorous tissue of prostate 14 which encroaches upon prostatic urethra 20 (causing constriction 15). In comparison, the temperature of prostate tissue adjacent to catheter second side 55 is generally controlled (e.g., below about 45° C.) to avoid necrosis of posterior tissues including ejaculatory duct 17 and rectum 18.

Transurethral thermal therapy treatment can include reaching intraprostatic temperatures of over 60° C. in tissue 26 surrounding prostatic urethra in the process of killing an adequately large area of tumorous prostatic tissue and returning patency to the prostatic urethra, even while cooling the urethral wall. Tissues rich in collagen, such as surrounding tissue 26, are subject to shrinkage when subject to temperatures greater than a predetermined collagen transition temperature (e.g. 60° C. to 70° C.) for a sufficient period of time, as described in the art. For an example of the time and temperature relationship for the shrinkage of collagen see, e.g., Gustavson, *The Chemistry and Reactivity of Collagen*, Academic Press, Inc., New York, 1956, and subsequent related articles known in the art.

To the extent that the collagen in the surrounding tissue 26 is not destroyed in the thermal therapy treatment and to the extent that the elevated intraprostatic temperatures (e.g. 60° C.) are maintained for a long enough period of time for the collagen in the surrounding tissue 26 to shrink, surrounding tissue 26 can shrink and constrict prostatic urethra 20. This shrinkage and constriction could partially negate the patency restoring effect of transurethral thermal therapy treatment.

However, collagen rich tissue can also be plastically modeled into a desired shape by shaping the surrounding tissue 26 while tissue 26 is at a temperature above its collagen transition temperature and then allowing the tissue to cool while in its desired shape until the temperature of the tissue is less than the collagen transition temperature. Accordingly, in the first method of the present invention, while the tumorous prostatic tissue including surrounding tissue 26 is at a temperature greater than a collagen transition temperature (e.g., during or after activating antenna 35 to necrose tumorous prostatic tissue), the inflated dilation and cooling balloon 36 dilates surrounding tissue 26 to prevent surrounding tissue 26 from shrinking about prostatic urethra 20. After the microwave energy source has been deactivated to terminate tile heating step, dilation and cooling of surrounding tissue 26 is maintained until surrounding tissue 26 cools to a temperature below the collagen transition temperature for a period of time sufficient for the collagen of surrounding tissue 26 to model itself based on the inflated shape of dilation and cooling balloon 36, so that tissue 26 is plastically reshaped to maintain patency of urethra 10. Dilation and cooling balloon 36 may be inflated during the heating step or after the heating step has been completed, while the temperature of surrounding tissue 26 is still above the collagen transition temperature, to dilate prostatic urethra 20 and surrounding tissue 26 and thereby plastically model the collagen rich tissue to maintain the desired diameter and shape of prostatic urethra 20 once the tissue cools. In an alternate embodiment, dilation and cooling balloon 36 may be omitted, and catheter 29 itself may be sized with a shape equal to the desired urethral shape, so that the collagen rich tissue surrounding the urethra is plastically remodeled to a shape based on the shape of catheter 29.

Once the surrounding tissues 26 have been allowed to return to normal body temperature (at least below a predetermined collagen transition temperature), the cooling system can be turned off thereby permitting deflation of dilation and cooling balloon 36 and cessation of circulation of cooling fluid. Once dilation and cooling balloon 36 and retention balloon 37 have been deflated, the catheter 29 can be removed from urethra 10.

The method of the present invention of performing a thermal therapy treatment on a prostate with catheter 29 while preventing collagen shrinkage about the urethra has considerable advantages. First, the method of the present invention incorporates a method and urethral catheter for treating BPH that uses preferential heating as described and illustrated in U.S. Pat. Nos. 5,413,588 and 5,628,770, amongst others. This preferential heating technique allows a greater amount of tissue anterior to the urethra to be substantially destroyed than tissue posterior to the urethra, thereby preserving the rectum and ejaculatory duct. Ablation of tumorous BPH tissue with this method restores patency to the urethra, among other therapeutic effects.

Second, the method of the present invention insures that the prostatic urethra is not inadvertently constricted by secondary effects of the transurethral thermal therapy treatment. For example, the first method dilates and cools the urethra and surrounding tissue during and/or after the thermal therapy treatment to prevent any collagen in the tissue surrounding the prostatic urethra from shrinking about the urethra to cause a constriction in the urethra. This preventive step ensures that urine flow, which is improved by transurethral thermal therapy, will not be compromised by inadvertent shrinkage of collagen rich tissue about prostatic urethra. Moreover, since the dilation and cooling step effectively remodels the collagen rich surrounding tissue into a selected shape having a desired expanded diameter, this step of the method can actually increase the patency of the prostatic urethra and surrounding tissue rather than just merely preventing shrinkage.

Figure 13:
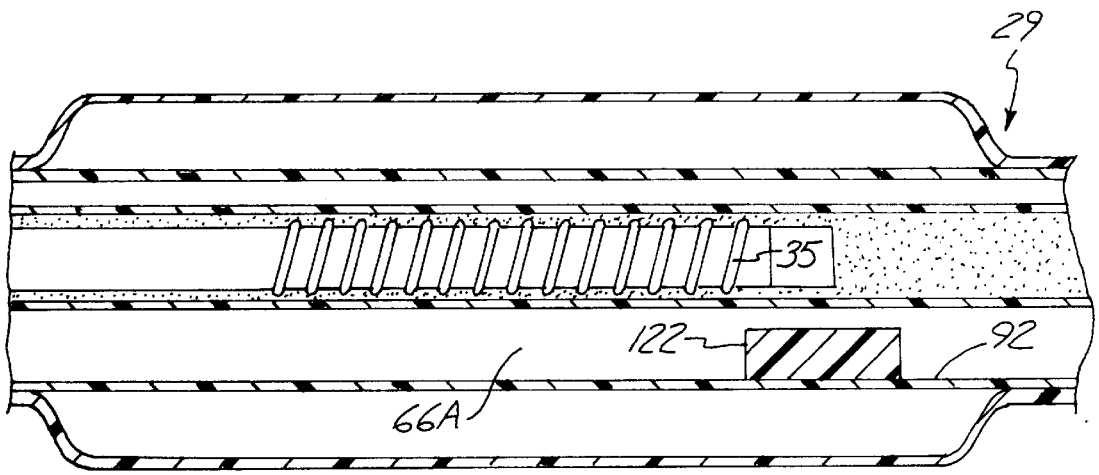
FIG. 13 is a sectional view of FIG. 10 as taken along lines 13—13.

In an alternative embodiment, catheter 29 can be modified to accentuate the circulation and inflation of cooling fluid within dilation and cooling balloon 36. FIG. 13 is a sectional view of catheter 29 in FIG. 10 as taken along lines 13—13. As shown in FIG. 13, catheter 29 further includes restriction 122 located distal to hole 92 within cooling exhaust lumen 66A. Restriction 122 is positioned on an outer wall of cooling exhaust lumen 66A at a location selected to create a pressure differential between holes 90 and 92 thereby causing passive inflation and active circulation of fluid through dilation and cooling balloon 36. Restriction 122 as shown in FIG. 13 is preferably located immediately adjacent hole 92 and proximal to antenna 35 so that restriction 122 does not affect near field radiation emitted by antenna 35. However, restriction 122 can be located at a more distal location adjacent antenna 35 if desired. Restriction 122 is formed and added to cooling exhaust lumen 66A by depositing adhesive on an inner surface of an outer wall of cooling exhaust lumen 66A at a desired location.

In use, cooling fluid passing through cooling exhaust lumen 66A enters cooling balloon 36 through hole 92 thereby permitting inflation of cooling balloon 36. Restriction 122 accentuates passive inflation of cooling balloon 36 and circulation of fluid therethrough by creating a pressure differential between holes 90 and 92. Hole 90 permits fluid to exit cooling balloon 36 into cooling exhaust lumens 66B for recirculation through a cooling system of catheter 120 (not shown).

Of course, if additional holes like holes 90 and 92 are formed in the side walls of cooling intake and exhaust lumens 64A–66B, additional restrictions like restriction 122 can be placed accordingly to further accentuate filling and circulation of fluid through dilation and cooling balloon 36.

Figure 14:
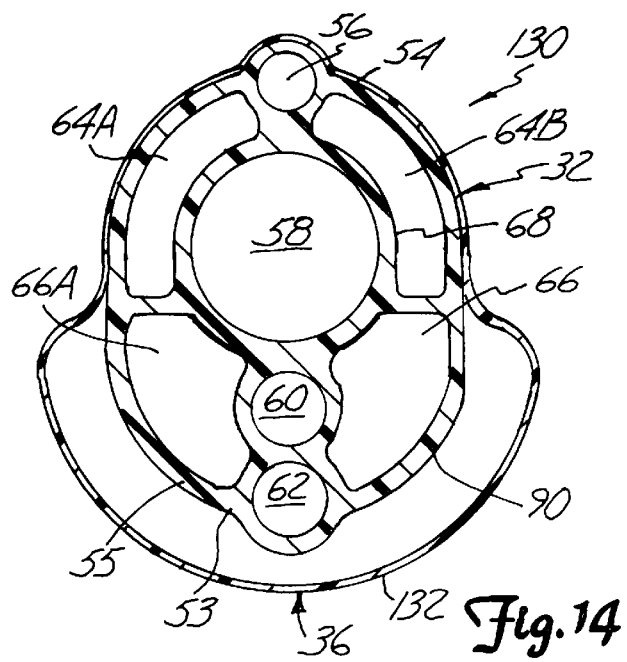
FIG. 14 is a sectional view of an alternate embodiment of the catheter of FIG. 4 taken along lines 14—14.

FIG. 14 is a transverse cross sectional view of an alternate embodiment of FIG. 4 taken along lines 14—14. FIG. 14 illustrates the alternate embodiment of catheter 130 having dilation and cooling balloon 132 configured to only partially surround a second side 55 of catheter shaft 32. Except for the modification of dilation and cooling balloon 132, catheter 130 has substantially the same attributes and features of catheter 29. Accordingly, the reference numerals used for catheter 29 are used in FIG. 14 to represent similar structures in catheter 130. Dilation and cooling balloon 132 is provided to permit asymmetric positioning of catheter 130 within urethra 10, thereby permitting selective orientation of radiation emitted from antenna 35 from catheter 130. The structure of catheter 130 is also substantially described and illustrated in the assignee's co-pending application Ser. No. 08/672,504, filed on Jun. 17, 1996 and titled DEVICE FOR TRANSURETHRAL THERMAL THERAPY WITH COOLING BALLOON.

Finally, a second alternative embodiment of catheter 29 is shown in FIG. 15 as catheter 140. FIG. 15 is a plan view of catheter 140. Catheter 140 includes substantially all of the features and attributes of catheter 29 and accordingly includes the same reference numerals as used for catheter 29 to refer to substantially similar structures or features in catheter 140. However, where catheter 140 includes differences from catheter 29, unique reference numerals are used to denote the structure.

First, as shown in FIG. 15, catheter 140 includes a shaft 141 arranged to cause antenna 35 to be aligned along a central longitudinal axis of shaft 141 instead of being aligned like antenna 35 in catheter 29 (FIG. 4) along an axis parallel to and spaced from the central longitudinal axis of shaft 141. This central axis alignment of antenna 35 is further illustrated in FIG. 16, which is a transverse cross sectional view of FIG. 15 taken along lines 16—16.

As shown in FIG. 16, catheter shaft 141 defines microwave antenna lumen 142 that carries antenna 35 along a central longitudinal axis of shaft 141. Catheter shaft 141 further defines retention balloon inflation lumen 144, urine drainage lumen 146, cooling intake fluid lumens 148A, 148B and cooling exhaust fluid lumens 150A, 150B. Catheter 140 does not include a dedicated temperature sensing lumen as found in catheter 29 (see lumen 56 in FIG. 5). In addition, cooling intake and exhaust lumens 148A–150B of catheter 140 substantially surround antenna lumen 142, each lumen having substantially the same transverse cross sectional area. With the absence of a temperature sensing lumen in catheter 140, the cooling lumens 148A–150B of catheter 140 have a larger total transverse cross-sectional area than the cooling lumens 64A–64B of catheter 29 (FIG. 5). This larger area permits even greater thermal conductive cooling and, if desired, near field microwave energy absorption when lumens 148A–150B are filled with a microwave absorbing fluid.

While catheter 140 does not include a dedicated temperature sensing lumen, catheter 140 does include a temperature sensing unit 154 as shown in FIG. 17. FIG. 17 is an enlarged sectional view of FIG. 16 taken along lines 17—17 and illustrating catheter shaft 141 proximally from the transverse cross section of FIG. 16.

As shown in FIG. 17, temperature sensor 154 includes shaft 155 and sensor 156. Sensor shaft 155 extends along the length of catheter shaft 141 through cooling intake lumen 148B. Temperature sensor shaft 155 further extends into dilation and cooling balloon 36 through hole 158 in side wall 160 defined in cooling intake lumen 148B (in a manner substantially similar to hole 91 shown in FIG. 8). Sensor 156 is adhesively bonded to an interior of the expandable wall 82 of dilation and cooling balloon 36 of catheter 140. Alternatively, the temperature of prostatic tissue may be monitored directly by an interstitial temperature sensor extending into the desired region of the prostate.

The centrally located microwave antenna lumen 142 results in a centrally located antenna which is beneficial in treating conduits and surrounding tissue not requiring preferential heating patterns that would be produced with the off axis antenna of catheter 29. This central alignment of antenna 35 is further accentuated by the substantially equal size and position of cooling intake lumens 148A,148B and cooling exhaust lumens 150A,150B. Moreover, placing sensor 156 along the interior of dilation and cooling balloon 36 permits more direct measurement of the temperature of prostatic urethra 20 or other conduit wall. Arranging temperature sensor shaft 155 to float within cooling intake lumen 148B avoids the need for a separate temperature sensing lumen in catheter shaft 141, thereby permitting cooling intake and exhaust lumens 148A–150B to have larger transverse cross sections and simplifying extrusion of catheter 140.

A second method of the present invention enables a thermal therapy treatment that ablates tumorous prostatic tissue and prevents shrinkage of collagen rich tissue surrounding the urethra without the need for dilation and cooling balloon. This method is illustrated in FIGS. 18–21.

FIG. 18 is a partial plan view of catheter 200 of the present invention. Catheter 200 has substantially the same features and attributes of catheter 29 (FIG. 4) except not including dilation and cooling balloon 36. Accordingly, catheter 200 is presented with the same reference numerals as used for catheter 29 to represent substantially similar features and attributes appearing catheter 200. As shown in FIGS. 19 and 20, catheter 200 includes temperature sensing lumen 56, antenna lumen 58, urine drainage lumen 60 and retention balloon inflation lumen 62 as well as cooling fluid intake and exhaust lumens 64A, 64B, 66A, 66B. Each of these lumens have the same structure as shown in FIG. 5 for catheter 29. However, since catheter 200 lacks a dilation and cooling balloon, cooling intake and exhaust lumens do not include any holes in their outer side walls (such as holes 90 and 92 for catheter 29 shown in FIG. 9) for communicating with such a balloon. Accordingly, catheter 200 has a structure substantially similar to the catheter shown in assignee's U.S. Pat. Nos. 5,628,770 and 5,413,588, which are both hereby incorporated by reference.

FIG. 21 is a vertical sectional view of a urethra shown with a catheter of FIG. 18 of the present invention positioned therein. As shown in FIG. 21, catheter 200 is positioned in urethra 10 so that retention balloon 37 is inflated in bladder 11 to secure catheter 200 relative to prostate 12, thereby positioning antenna 35 adjacent target tissue 100. Once properly positioned, catheter 200 is used to thermally ablate tumorous prostatic tissue 100 as substantially described and illustrated in U.S. Pat. Nos. 5,413,588 and 5,628,770.

With catheter 200 properly positioned, antenna 35 is energized with a microwave energy generating source (connected via manifold 30) to cause microwave radiation to be emitted radially from antenna 35 into tissue 26 the targeted prostatic tissue (e.g., 100) including tissue 26 surrounding antenna 35. The microwave radiation is applied at frequencies of 902–928 MHZ and at a power and for a time sufficient to inductively heat prostatic tissue according to a time and temperature relationship (previously described herein) to heat targeted tissue above 45° C. for a period of time sufficient to substantially destroy the tumorous tissue. Cooling fluid circulating through cooling fluid intake and exhaust lumens 64A, 64B, 66A and 66B cools prostatic urethra 20 to preserve urethra 10 during the heating step of the thermal therapy treatment.

However, in this embodiment of the present invention, the temperature of prostatic tissue and the length of treatment are monitored to ensure that the temperature of tissue 26 surrounding prostatic urethra 20 does not exceed a predetermined collagen transition temperature of the surrounding tissue 26 (e.g. 60° C.). This controlled therapy prevents shrinkage of the non-destroyed portion of tissue 26 about prostatic urethra 20 that would otherwise occur due to the natural shrinkage of collagen rich tissue that occurs when tissue 26 is exposed to temperatures above a collagen transition temperature. With the assignee's catheter 200, the prostatic temperatures are reliably inferred by monitoring with a temperature sensing unit in temperature sensing lumen. The power applied to the microwave energy source and the antenna and/or the rate and temperature of cooling fluid flow are controlled as necessary to maintain an appropriate time and temperature relationship sufficient to necrose the tumorous tissue while maintaining the temperature of surrounding tissue 26 below a collagen transition temperature.

This method of the present invention has several advantages. First, this method incorporates a method and urethral catheter for treating BPH that uses preferential heating as described and illustrated in U.S. Pat. Nos. 5,413,588 and 5,628,770, amongst others. This preferential heating technique allows a greater amount of tissue anterior to the urethra to be substantially destroyed than tissue posterior to the urethra, thereby preserving the rectum and ejaculatory duct. Ablation of tumorous BPH tissue with this method restores patency to the urethra, among other therapeutic effects.

Second, this method of the present invention ensures that the prostatic urethra is not inadvertently constricted by secondary effects of the transurethral thermal therapy treatment. Foremost, the method controls the temperature of the surrounding tissue 26 to a temperature below the collagen transition temperature during the thermal therapy treatment to prevent any collagen in the tissue surrounding the prostatic urethra from shrinking about the urethra to cause a constriction in urethra. This preventive step insures that urine flow, which is improved by transurethral thermal therapy, will not be compromised by inadvertent shrinkage of collagen rich tissue about prostatic urethra. In addition, this method may diminish undesired immunologic response which can occur at higher temperatures (e.g. 60° C. to 70° C.).

The antenna illustrated and described in U.S. Pat. Nos. 5,300,099 and 5,370,677, which are hereby incorporated by reference, can be used in catheter 10 (in place of the antenna of FIG. 6) when appropriately sized.

The previously described principles, including a time and temperature relationship for causing collagen shrinkage, known to those skilled in the art are applied to cool and/or maintain dilation of collagen rich tissue for a time sufficient to prevent collagen shrinkage for the given age and/or type of tissue.

The method of the present invention permits thermal therapy treatment of tumorous prostatic tissue adjacent a urethra while preventing restrictions of the urethra due to heat-induce shrinkage of collagen rich tissue surrounding the urethra. Thus, normal functioning of the urethra is achieved by maintaining the original diameter of the urethra in combination with another treatment (transurethral thermal therapy) of the prostatic tissue adjacent the urethra. Functional use of the conduit is restored without conventional surgery and without sacrificing any portion of the urethra or remote portion of the body to supply a replacement section of urethra.

More specifically, and quite significantly, a first method of the present invention of dilating collagen rich tissue to prevent constriction of a urethral diameter is used to improve patency of the urethra after a transurethral thermal therapy treatment, thereby further improving patient conditions, such as urine flow, after ablation of the tumorous tissue of BPH. This ensures that the prostatic urethra is not inadvertently constricted by secondary effects of the transurethral thermal therapy treatment. The first method defines a selected shape of the urethra, such as by dilation, and cools the urethra and surrounding tissue during and/or after the thermal therapy treatment to prevent any collagen in the tissue surrounding the prostatic urethra from shrinking about the urethra to cause a constriction in urethra. Alternatively, a second method of the invention similarly ensures that the prostatic urethra is not constricted by secondary effects of transurethral thermal therapy by preventing the collagen rich tissue surrounding the urethra from being heated to a temperature exceeding a predetermined collagen transition temperature. These preventive steps insure that urine flow, which is improved by transurethral thermal therapy, will not be compromised by inadvertent shrinkage of collagen rich tissue about prostatic urethra. Moreover, since the dilation and cooling step of the first method effectively plastically remodels the collagen rich surrounding tissue into a selected shape having a desired expanded diameter, this step of the first method can increase the patency of the prostatic urethra and surrounding tissue by increasing a urethral diameter, rather than just merely preventing shrinkage.

Although the present invention has been described with reference to preferred embodiments, workers skilled in the art will recognize that changes may be made in form and detail without departing from the spirit and scope of the invention.

What is claimed is:

1. A method of treating benign prostatic hyperplasia comprising:

heating a select volume of prostatic tissue surrounding the urethra to a temperature above about 45° C. for a time sufficient to substantially destroy the select volume of tissue and a collagen-containing portion of the select volume to a temperature above a predetermined collagen transition temperature of about 60° C. for a time sufficient to cause the collagen-containing portion of the select volume to be capable of being plastically remodeled;

defining a selected shape of the urethra while the collagen-containing portion of the select volume of tissue is at the temperature above the predetermined collagen transition temperature; and allowing the collagen-containing portion of the select volume of tissue to cool to a temperature below the predetermined collagen transition temperature while continuing to define the selected shape of the urethra for a time sufficient to cause plastic remodeling of the collagen-containing portion of the select volume of tissue.

2. The method of claim 1 wherein the step of defining the selected shape of the urethra includes dilating the urethra to the selected shape.

3. The method of claim 2 wherein the step of dilating the urethra includes inflating a dilation balloon in the urethra.

4. The method of claim 1 wherein the step of defining the selected shape of the urethra includes locating within the urethra a catheter defining the selected shape.

5. A method of treating benign prostatic hyperplasia comprising:

heating prostatic tissue for a time sufficient to produce and maintain a temperature above a threshold temperature of about 60° C. for remodeling collagen in a select volume of the prostatic tissue surrounding the urethra;

dilating the urethra to compress the select volume of tissue; and allowing the select volume of tissue to cool to a temperature below the threshold temperature for remodeling collagen while dilating the urethra for a sufficient period of time to plastically remodel the select volume of tissue.

6. A method of treating benign prostatic hyperplasia comprising:

inserting a probe within a urethra to position a microwave antenna within the probe adjacent to a prostate adjacent the urethra;

heating the prostate, while cooling the urethra, with microwave radiation from the microwave antenna to a temperature of at least about 45° C. for a time sufficient to substantially destroy a select volume of tissue within the prostate surrounding the urethra and to a temperature above a predetermined collagen transition temperature of about 60° C. in a collagen-containing portion of the select volume of tissue surrounding the urethra for a time sufficient to permit collagen remodeling;

dilating the urethra while maintaining the collagen-containing portion of the select volume of tissue at a temperature above the predetermined collagen transition temperature; and allowing the collagen-containing portion of the select volume of tissue to cool, while maintaining dilation, until a temperature of the collagen-containing portion of the select volume of tissue is less than the predetermined collagen transition temperature for a time sufficient to cause plastic remodeling of the collagen-containing portion of the select volume of tissue.

* * * * *